US012472105B2

United States Patent
(12) United States Patent
Hoffman et al.

(10) Patent No.: US 12,472,105 B2
(45) Date of Patent: Nov. 18, 2025

(54) FOAM SLEEVE GARMENT WITH EASY ACCESS FEATURE

(71) Applicant: SIGVARIS AG, St. Gallen (CH)

(72) Inventors: Keith Hoffman, Hamilton, MI (US); Laure Kuipers, Holland, MI (US)

(73) Assignee: SIGVARIS AG, St. Gallen (CH)

( * ) Notice: Subject to any disclaimer, the term of this patent is extended or adjusted under 35 U.S.C. 154(b) by 245 days.

(21) Appl. No.: 18/027,335

(22) PCT Filed: Nov. 10, 2021

(86) PCT No.: PCT/US2021/058795
§ 371 (c)(1),
(2) Date: Mar. 20, 2023

(87) PCT Pub. No.: WO2022/103850
PCT Pub. Date: May 19, 2022

(65) Prior Publication Data

US 2024/0058177 A1 Feb. 22, 2024

Related U.S. Application Data

(60) Provisional application No. 63/111,906, filed on Nov. 10, 2020.

(51) Int. Cl.
*A61F 13/00* (2024.01)
*A61F 13/08* (2006.01)
*A61F 13/10* (2006.01)

(52) U.S. Cl.
CPC ............ *A61F 13/08* (2013.01); *A61F 13/107* (2013.01)

(58) Field of Classification Search
USPC ..................................................... 602/62, 64
See application file for complete search history.

(56) References Cited

U.S. PATENT DOCUMENTS 5,743,866 A 4/1998 Bauerfeind et al.
6,254,554 B1 * 7/2001 Turtzo .................. A61F 13/085 601/134
9,125,787 B2 9/2015 Malhi et al.
2007/0276310 A1 11/2007 Lipshaw et al.

OTHER PUBLICATIONS

Sigvaris AG; International Application No. PCT/US2021/058795 filed Nov. 10, 2021; International Search Report and Written Opinion; ISA/US; Jan. 31, 2022; 8 pp.

* cited by examiner

*Primary Examiner* — Kim M Lewis
(74) *Attorney, Agent, or Firm* — FisherBroyles LLP; Anthony J DoVale

(57) ABSTRACT

A chip sleeve garment including an outer layer of fabric connected to an inner layer of fabric to form a sleeve with a space between the outer layer of fabric and the inner layer of fabric. Foam chips, flat foam, or foam with ridges are disposed in the space between the outer layer of fabric and the inner layer of fabric. The garment includes two ends, including at least one open end, and a notch in at least one open end having an opening. The notch can be separated to create a larger opening than the opening to allow the garment to be donned or doffed easier than the opening allows. A second garment can be disposed over the chip sleeve garment. Either the chip sleeve garment, the second garment, or both can be compression garments.

19 Claims, 12 Drawing Sheets

FOAM SLEEVE GARMENT WITH EASY ACCESS FEATURE

In one aspect, the present disclosure details liners or compression garments, including lymphedema compression garments, which are typically used for maintenance after the patient's limb has been decongested and stabilized. In at least one embodiment, the liner or garment comprises a chip sleeve portion including an inner and outer layer of fabric filled with "foam chips". In another embodiment, the liner or garment can be filed with a flat foam or a foam with ridges. In at least one embodiment, the liner or garment generally can be formed in a tubular shape with two open ends, but either of the two open ends can be closed or narrowed as desired. Generally, the liner or garment includes an inner layer and an outer layer that are generally stitched together to form spaced apart channels of foam chip ridges. In at least one embodiment, the chip sleeve is sewn or otherwise secured into a shape having an opening at the top and the bottom that can be slid over a limb, wrist, ankle, foot, or hand. The chip sleeve can have a notch along at least one end that allows the end to expand during donning or doffing. The liner or garment can be formed from a fabric or other material allowing the functionality detailed herewithin and shown in the figures. In at least one embodiment, the liner or garment can be formed from an elastic fabric to provide a range of size accommodation by virtue of its stretch properties.

BRIEF DESCRIPTION OF THE DRAWINGS

The accompanying drawings, which are incorporated herein and constitute part of this specification, illustrate the presently preferred embodiments of the disclosure, and, together with the general description given above and the detailed description given below, serve to explain the features of the disclosure. In the drawings.

DETAILED DESCRIPTION

Figure 1:
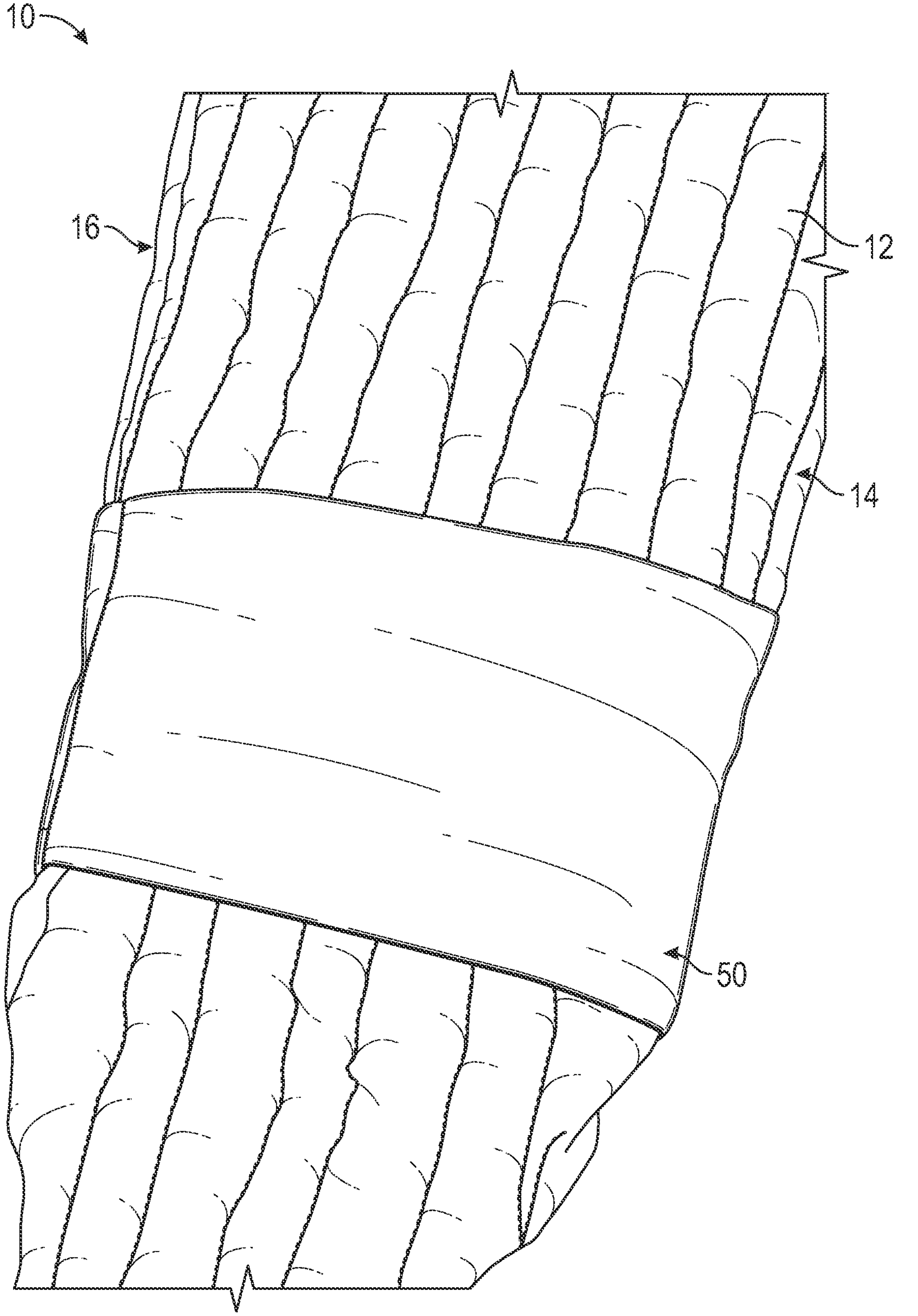
FIG. 1 shows an exemplary chip sleeve compression garment.

In the drawings, like numerals indicate like elements throughout. Certain terminology is used herein for convenience only and is not to be taken as limiting. The terminology includes the words specifically mentioned, derivatives thereof and words of similar import. The embodiments illustrated below are not intended to be exhaustive or to limit to the precise form disclosed. These embodiments are chosen and described to best explain the principles, application, and practical use, and to enable others skilled in the art to best utilize the present disclosure.

Figure 2:
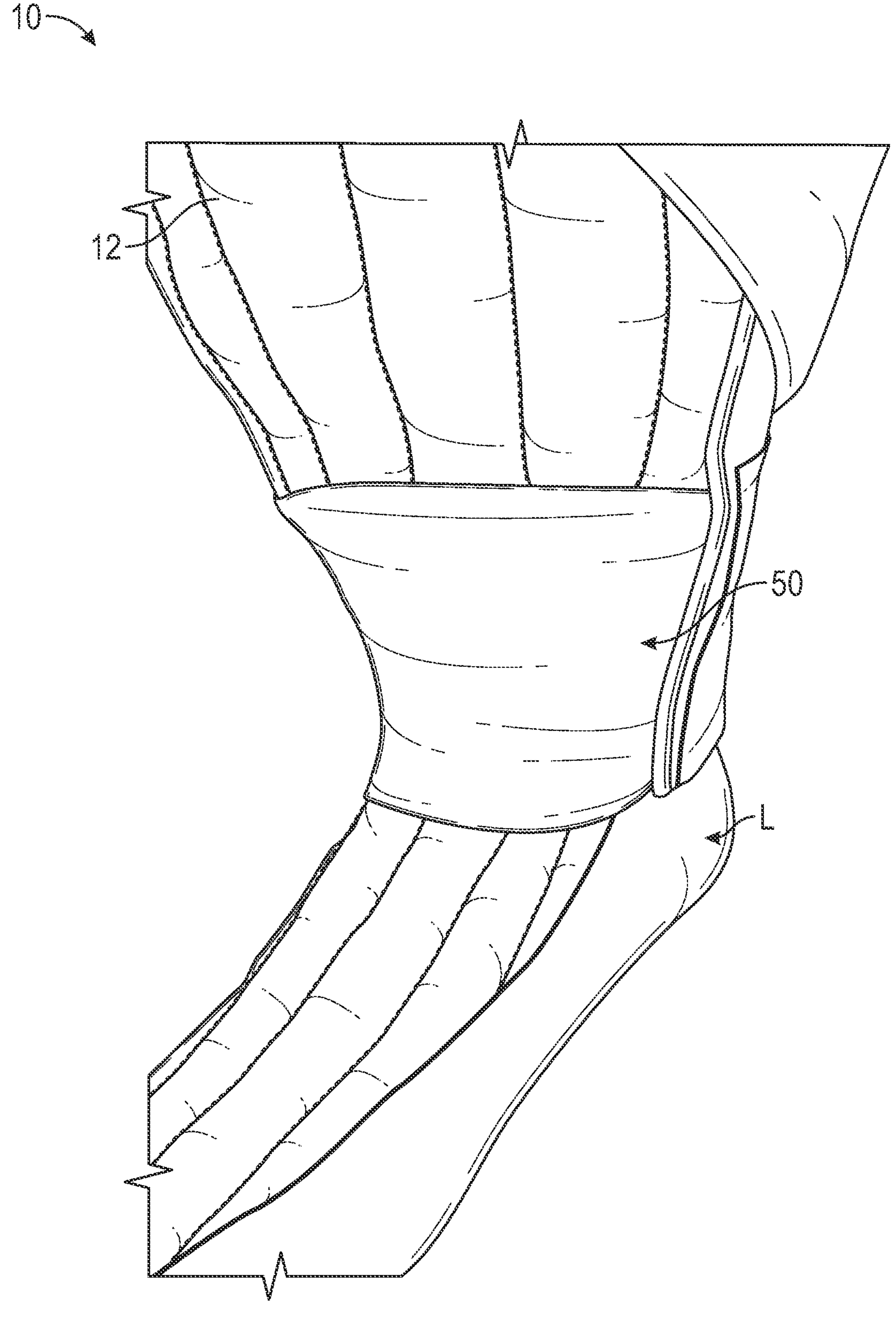
FIG. 2 shows the chip sleeve compression garment of FIG. 1 in place on a leg above an ankle of a user.
Figure 6:
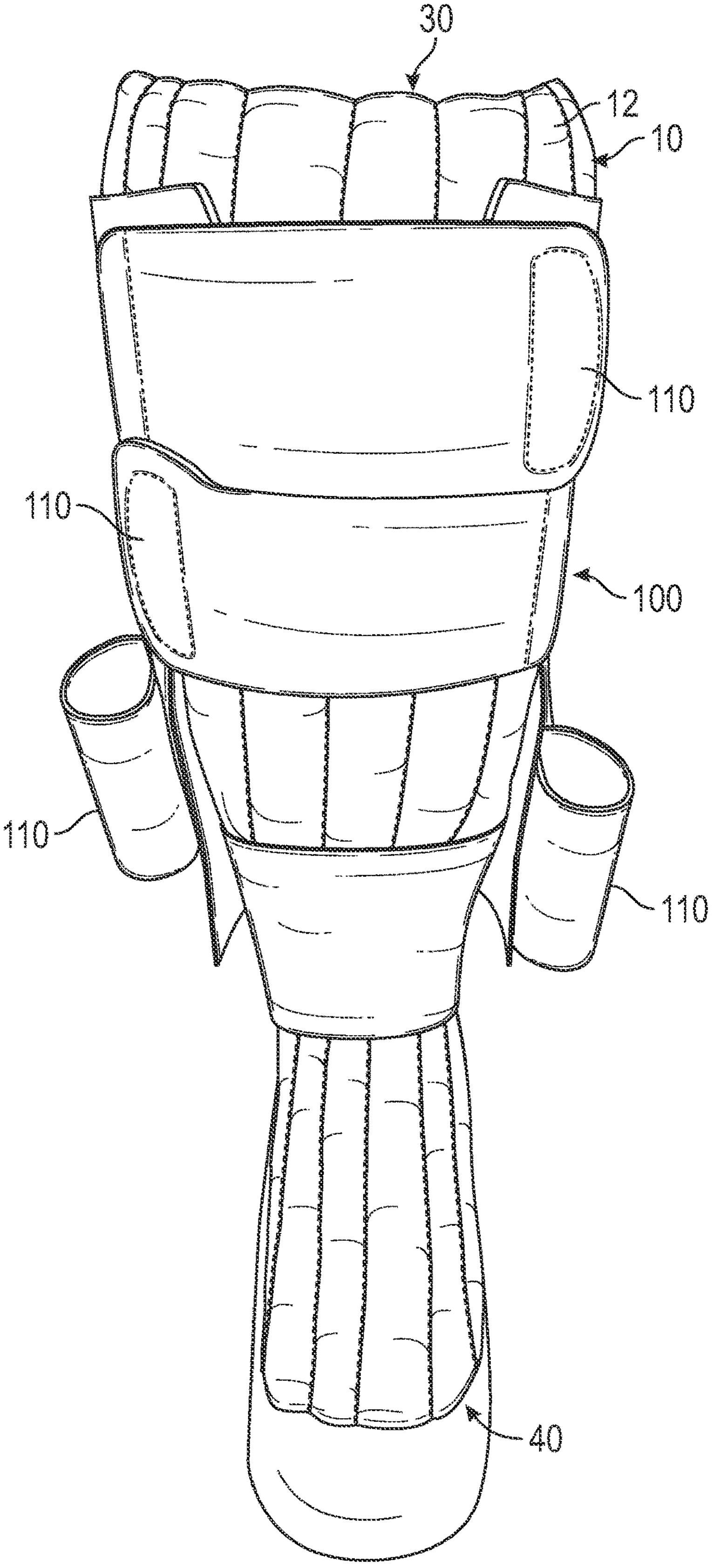
FIG. 6 shows the combined compression garments of FIG. 5 with two of the adjustment straps of the second compression garment in the open position.
Figure 7:
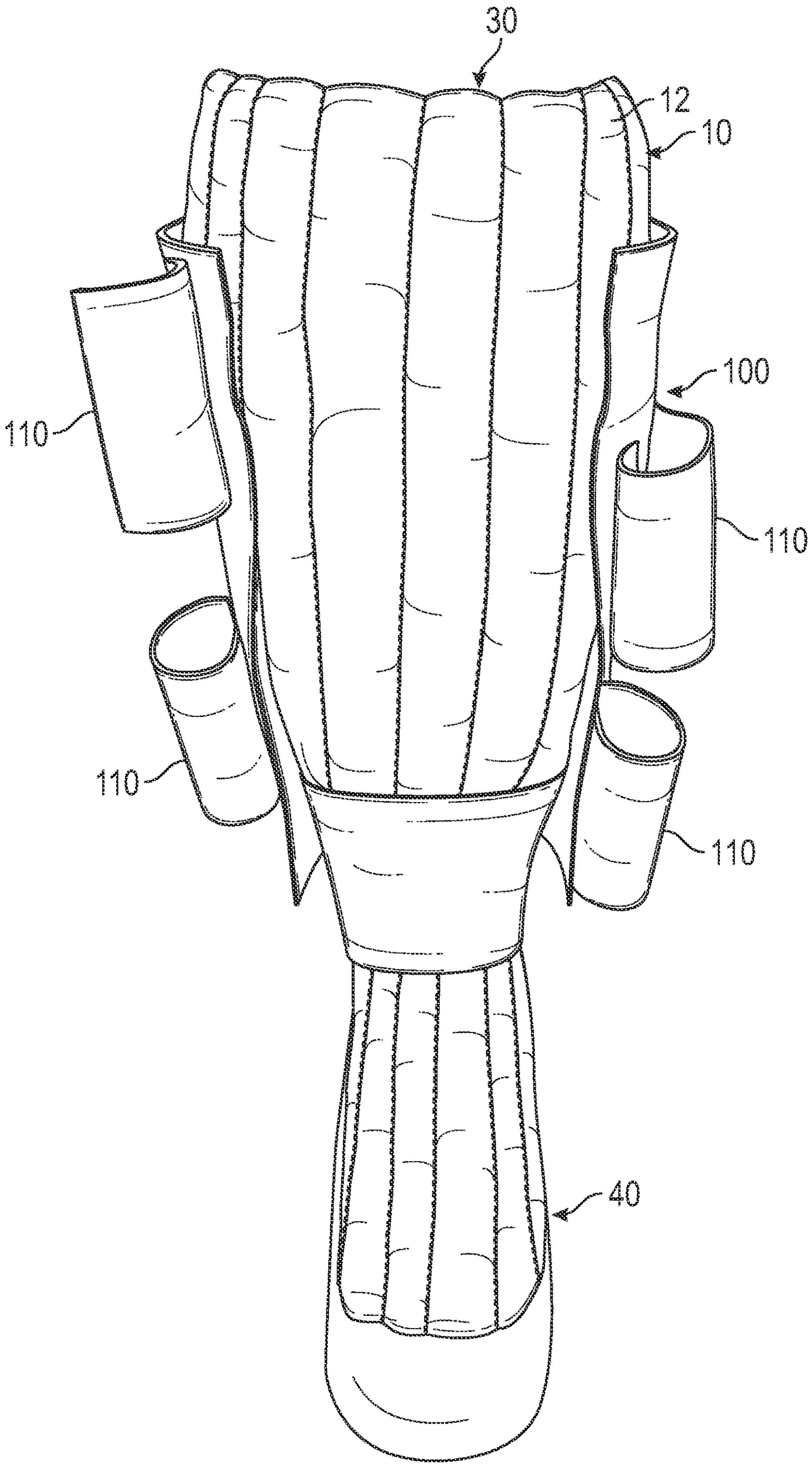
FIG. 7 shows the combined compression garments of FIG. 5 with all of the adjustment straps of the second compression garment in the open position.

FIG. 1 shows an exemplary chip sleeve compression garment 10. The garment 10 is shown as a sleeve 12 with two open ends 30, 40 (see FIG. 5) and with a medial portion 14 and a lateral portion 16. Generally, the garment 10 is disposed on an extremity, including an upper extremity, a lower extremity, or limb L, such as an arm or leg. As shown in FIG. 2, the chip sleeve compression garment 10 of FIG. 1 is disposed in place on a leg above an ankle of a user. The chip sleeve compression garment 10 can be a liner, or can either be used by itself or can be used in combination with other garments, including other compression garments, as shown in FIG. 5-7.

Figure 3:
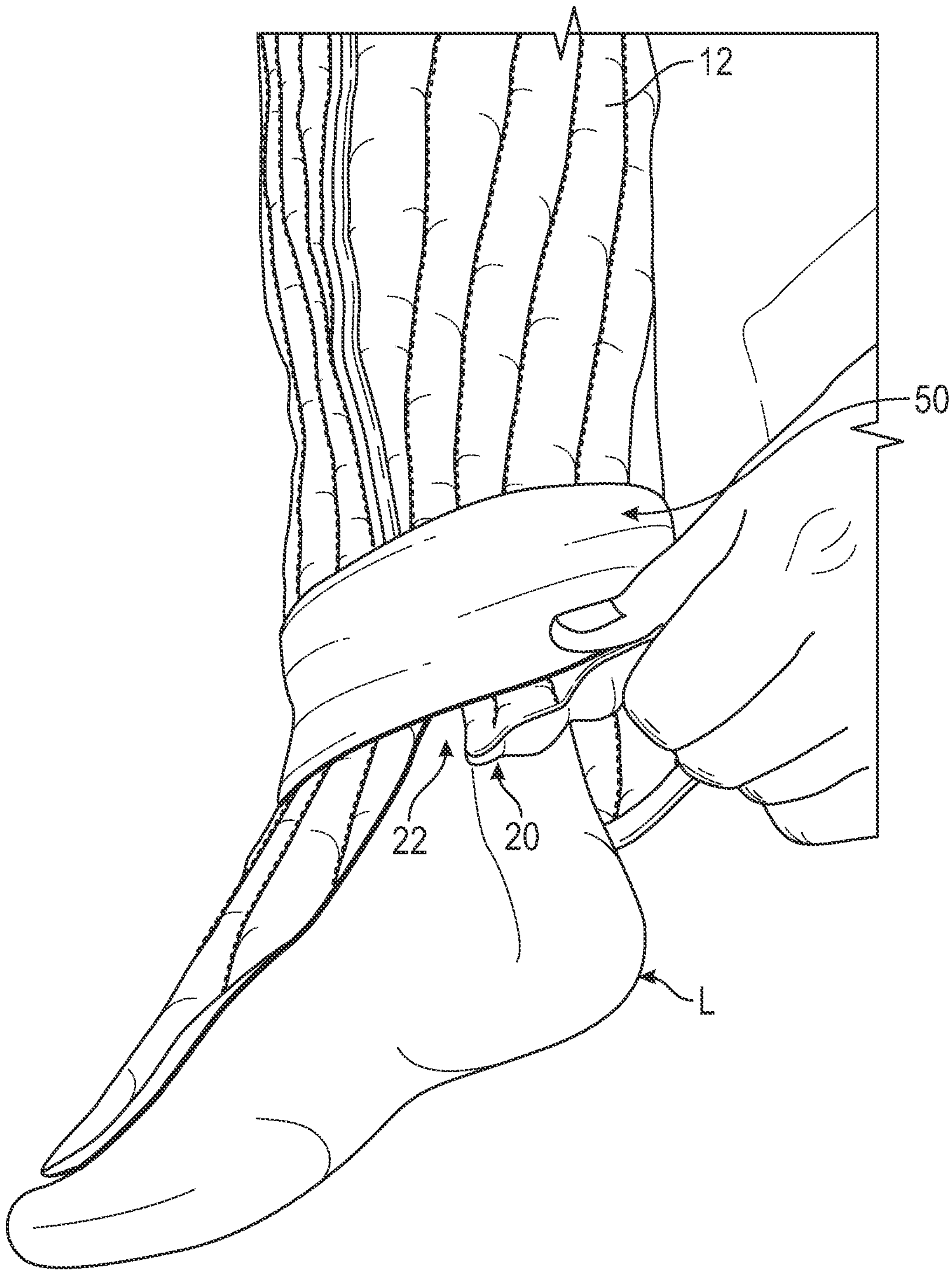
FIG. 3 shows the chip sleeve compression garment of FIG. 2 with an elastic stretch panel loop portion revealing a notch on a medial portion of the garment.

One aspect of the present disclosure includes a notch 20 or other open portion, shown at open end 40 of the garment 10. In the figures, the notch 20 is disposed on the medial portion 14, but the notch 20 could be included either on the lateral portion 16 or both on the medial portion 14 and lateral portion 16, or at any other position as desired, including along or otherwise at another portion of the garment 10. When disposed on the medial portion 14 as shown in FIG. 3, the opening or notch 20 can be used to facilitate donning or doffing the garment 10 from the user's limb L. The opening or notch 20 provides a wider opening portion (indicated in FIG. 3 at 22) to allow for easier fitting on a limb L, including over a wrist, ankle, foot, or hand, or removal from such. For example, the garment 10 could advantageously be designed to closely fit the size of a person's wrist, but the wrist portion of the garment 10 must expand over the hand as the garment 10 is donned and doffed. Similarly, the garment 10 could advantageously be designed to closely fit the size of a person's ankle, the ankle portion of the garment 10 must expand over the foot and heel as the garment 10 is donned and doffed. Additionally, as shown in FIG. 3, an elastic stretch panel loop portion 50 can be included proximate the opening or notch 20, which, among other benefits, can help keep the opening or notch 20 closed together when the user desires to keep the garment 10 in place on the limb L. The stretch panel 50 preferably is constructed from a material having a lower modulus of elasticity than the fabric comprising the chip sleeve compression garment 10, so that the force to expand the end 40 or portion of the chip sleeve garment 10 having the notch 20 is less than the force to expand the compression garment 10 otherwise fashioned without a notch 20, whereby making it easier to don and doff the garment 10.

Figure 4:
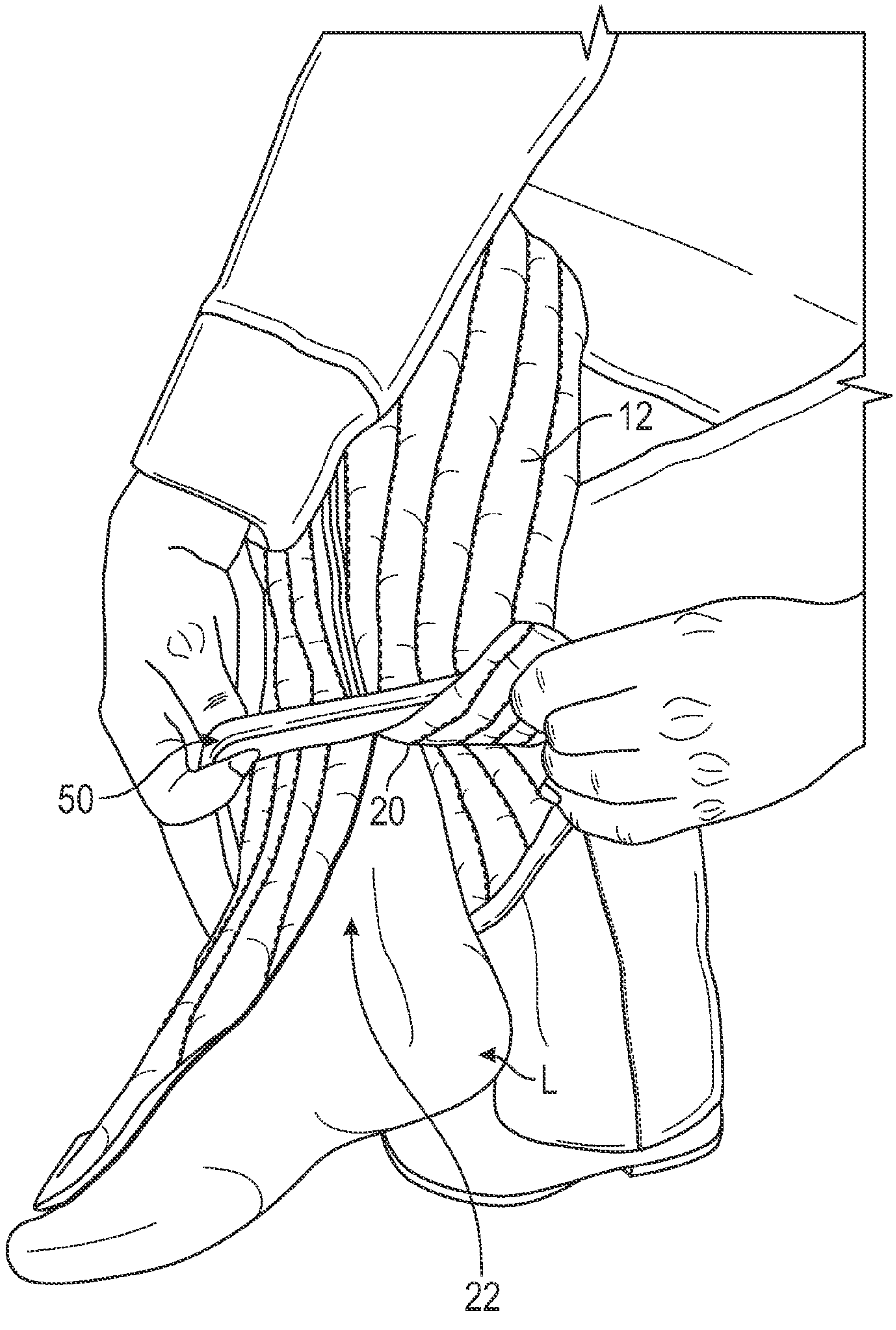
FIG. 4 shows the chip sleeve compression garment of FIG. 3 with the notch entirely opened and elastic stretch panel loop portion opened wide.

FIG. 4 shows the chip sleeve compression garment 10 of FIG. 3 with the notch 20 entirely opened and elastic stretch panel loop portion 50 opened wide to permit viewing the underlying notch 20. As shown in FIG. 4, the garment 10 is able to be removed from the limb L with the notch 20 providing a larger opening portion 22 than a garment 10 without such notch 20. Alternatively, the wider opening 22 of the elastic stretch panel loop portion 50 can ease adjustment of the garment 10 on the limb L of the user to move the garment 10 closer or further from the ankle, or to otherwise facilitate adjustment of the garment 10.

Figure 5:
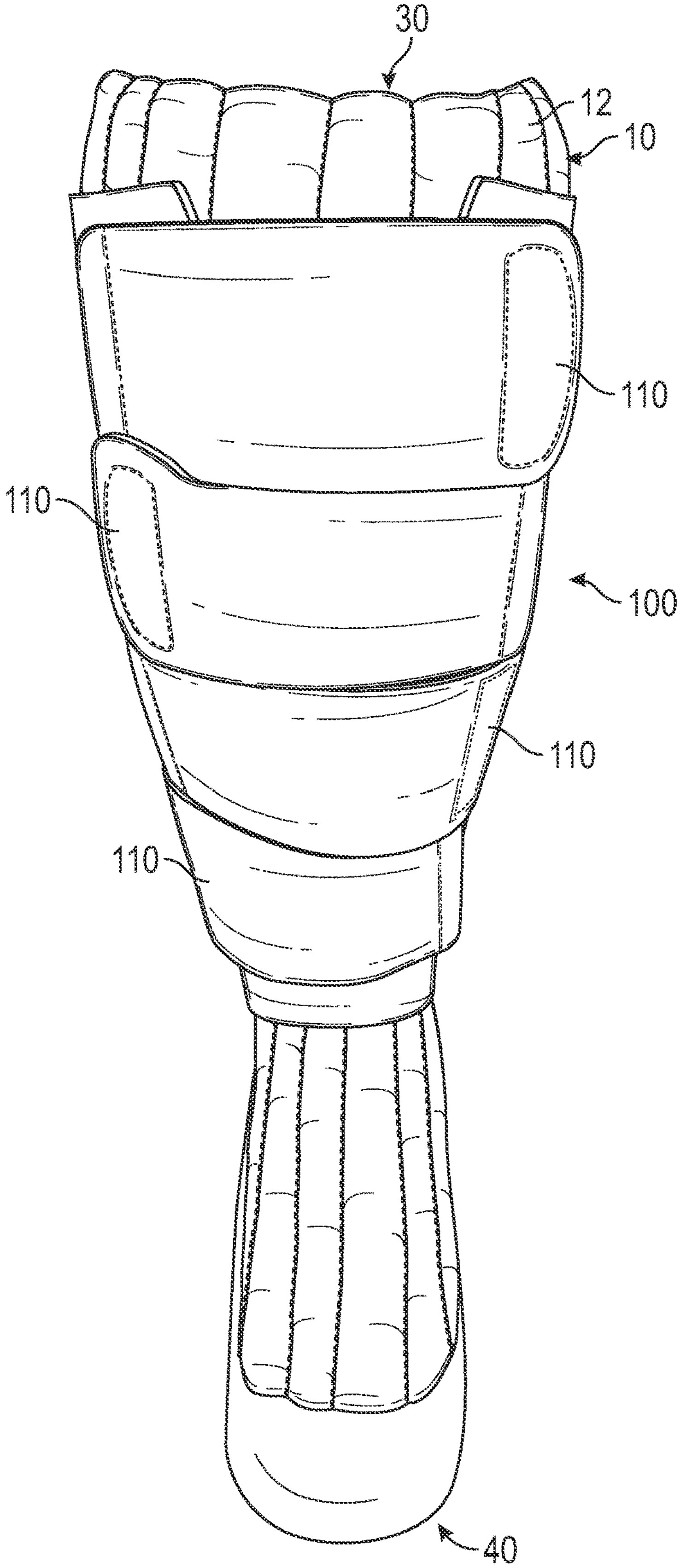
FIG. 5 shows the chip sleeve compression garment of FIG. 2 on a leg form combined with a second compression garment disposed on top of the chip sleeve compression garment.
Figure 8:
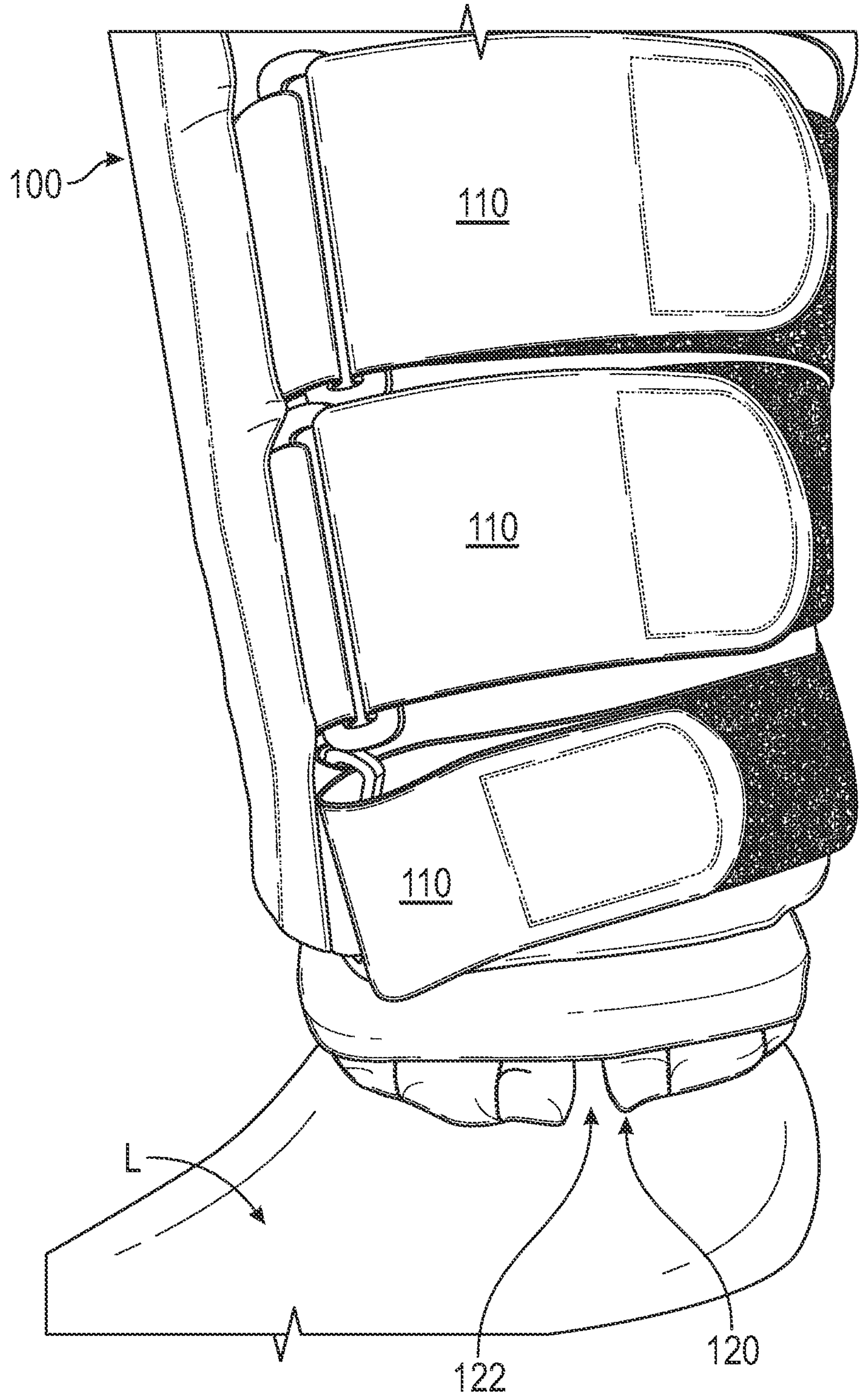
FIG. 8 shows a chip sleeve garment under a wrap with buckles and straps.

FIG. 5 shows the chip sleeve compression garment 10 of FIG. 3 being used in combination with a second compression garment 100 positioned over it. The second compression garment 100 as shown in FIGS. 5-7 includes adjustment straps 110 that allow the second compression garment 100 to be tightened or loosened as desired. FIG. 6 shows the combined compression garments 10, 100 of FIG. 5 with two of the adjustment straps 110 of the second compression garment 100 in an open position, revealing the stretch panel portion 50 of the chip sleeve compression garment 10 proximate the ankle portion of the limb L. The stretch panel portion 50 acts to close the notch 20 in the chip sleeve compression garment 10 so that the chip sleeve garment 10 fully encircles the limb L. FIG. 7 shows the combined compression garments 10, 100 of FIG. 5 with all adjustment straps 110 of the second compression garment 100 in the open position. In another exemplary embodiment, a chip sleeve can be used with a Compreflex Reduce garment, such as the garment detailed in U.S. Pat. No. 10,820,648, which is incorporated by reference herein. Here, the chip sleeve would include a different connection in a rear location, but essentially function similarly to the chip sleeve detailed herewithin. FIG. 8 shows a side view of a liner similar to the chip sleeve shown in FIGS. 5-7 but does not include a portion to cover an upper part of a foot and instead ends with a notch 120 to provide a wider opening 122 adjacent an ankle of a user when donned.

Figure 9:
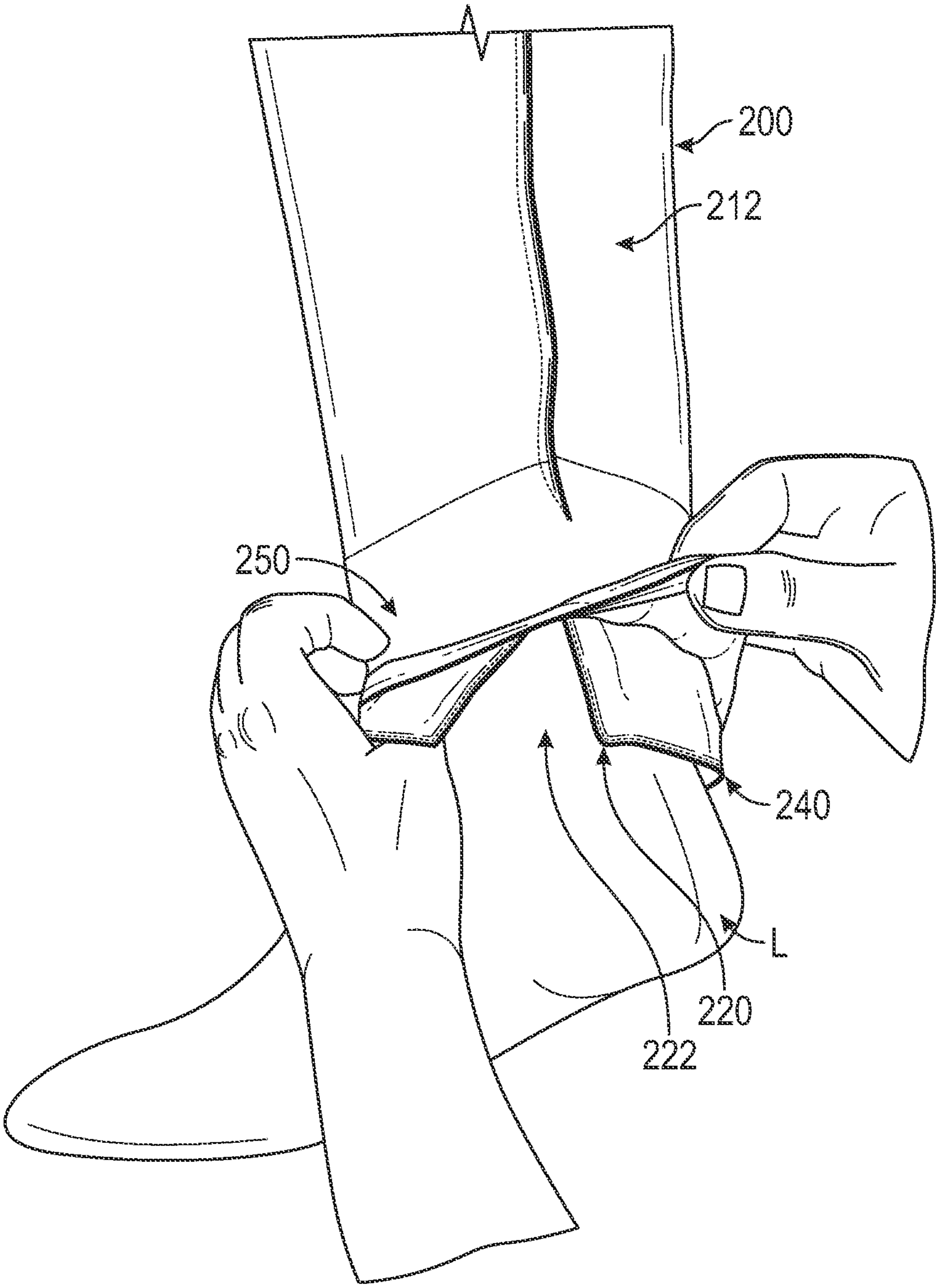
FIG. 9 shows a foam liner having flat foam or foam with ridges and a notch with an elastic stretch panel loop.
Figure 10:
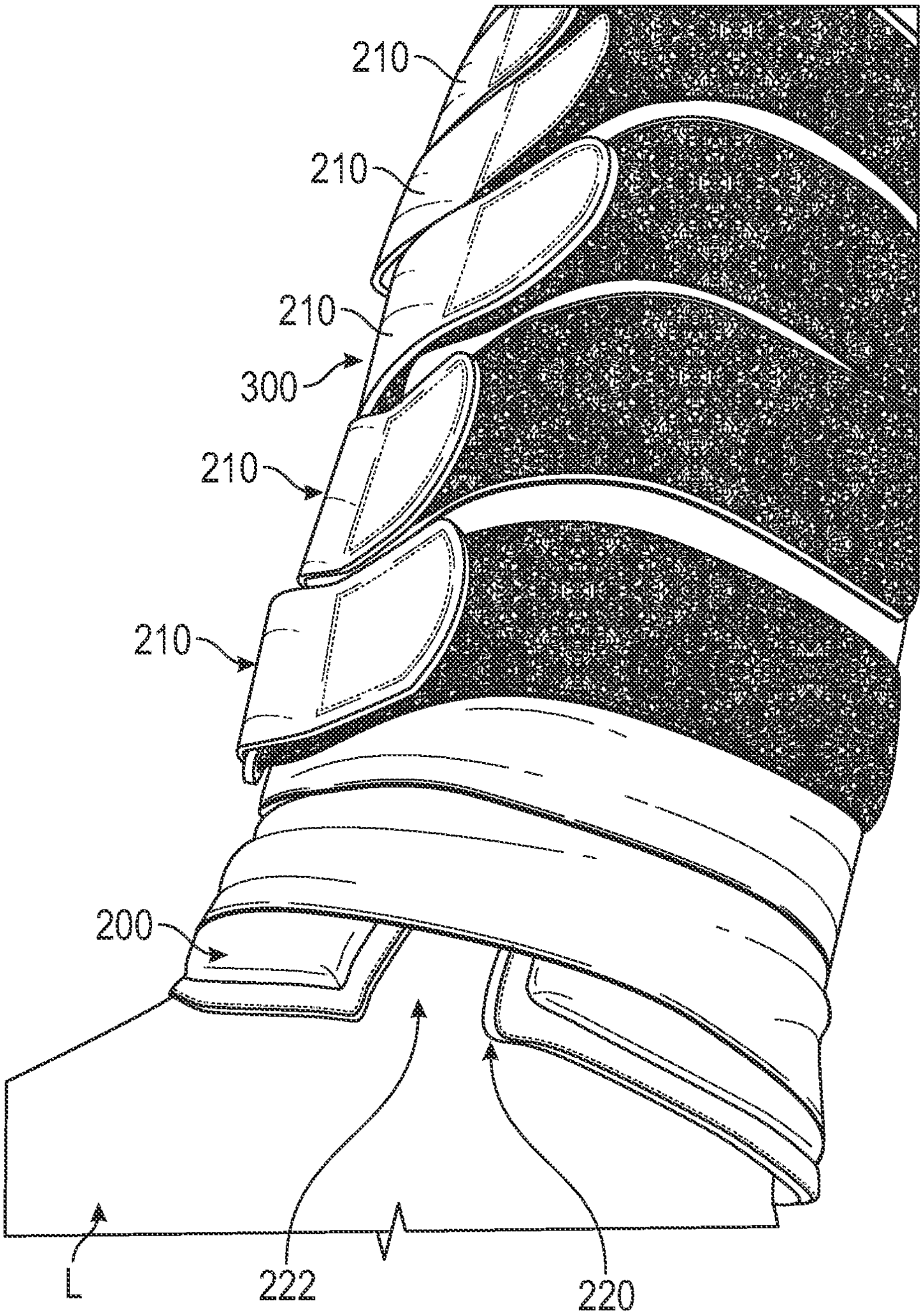
FIG. 10 shows the foam liner of FIG. 9 combined with a second compression garment disposed over it.
Figure 11:
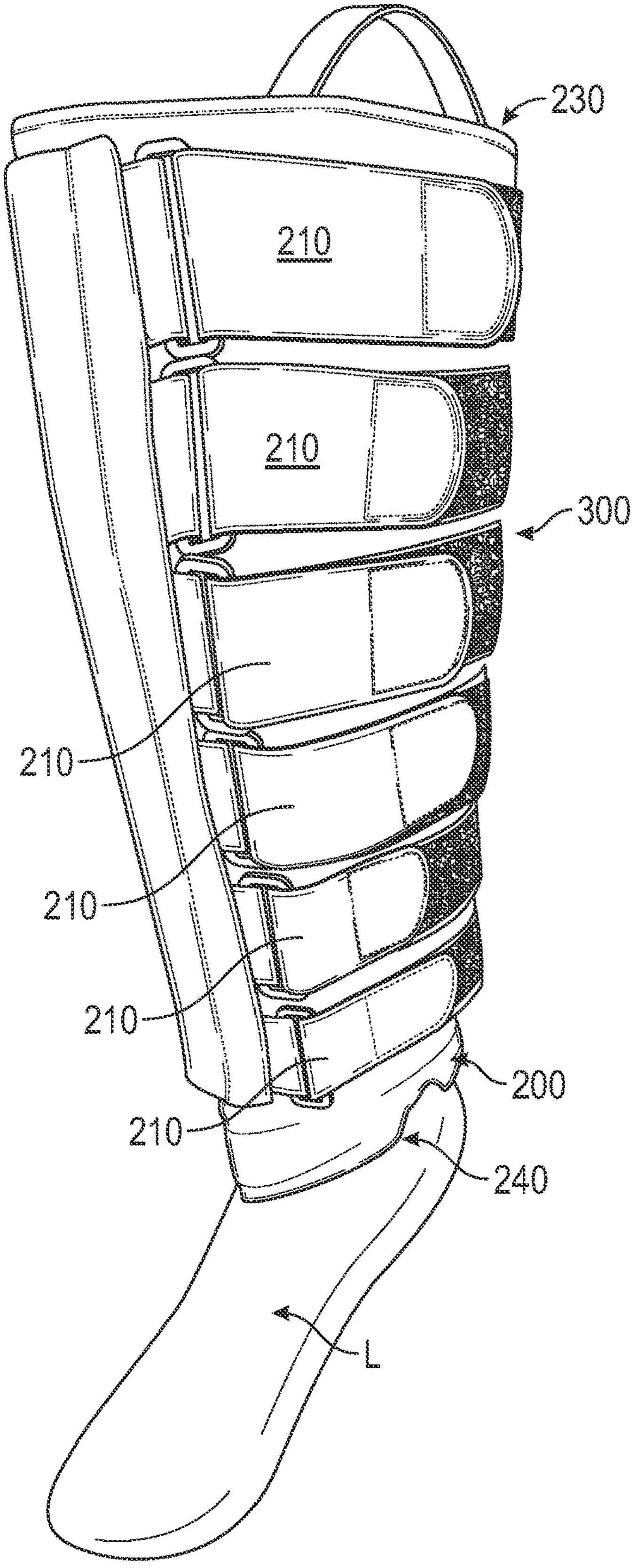
FIG. 11 shows the foam liner of FIG. 10 having a flat foam and a notch feature under a wrap having buckles and straps.
Figure 12:
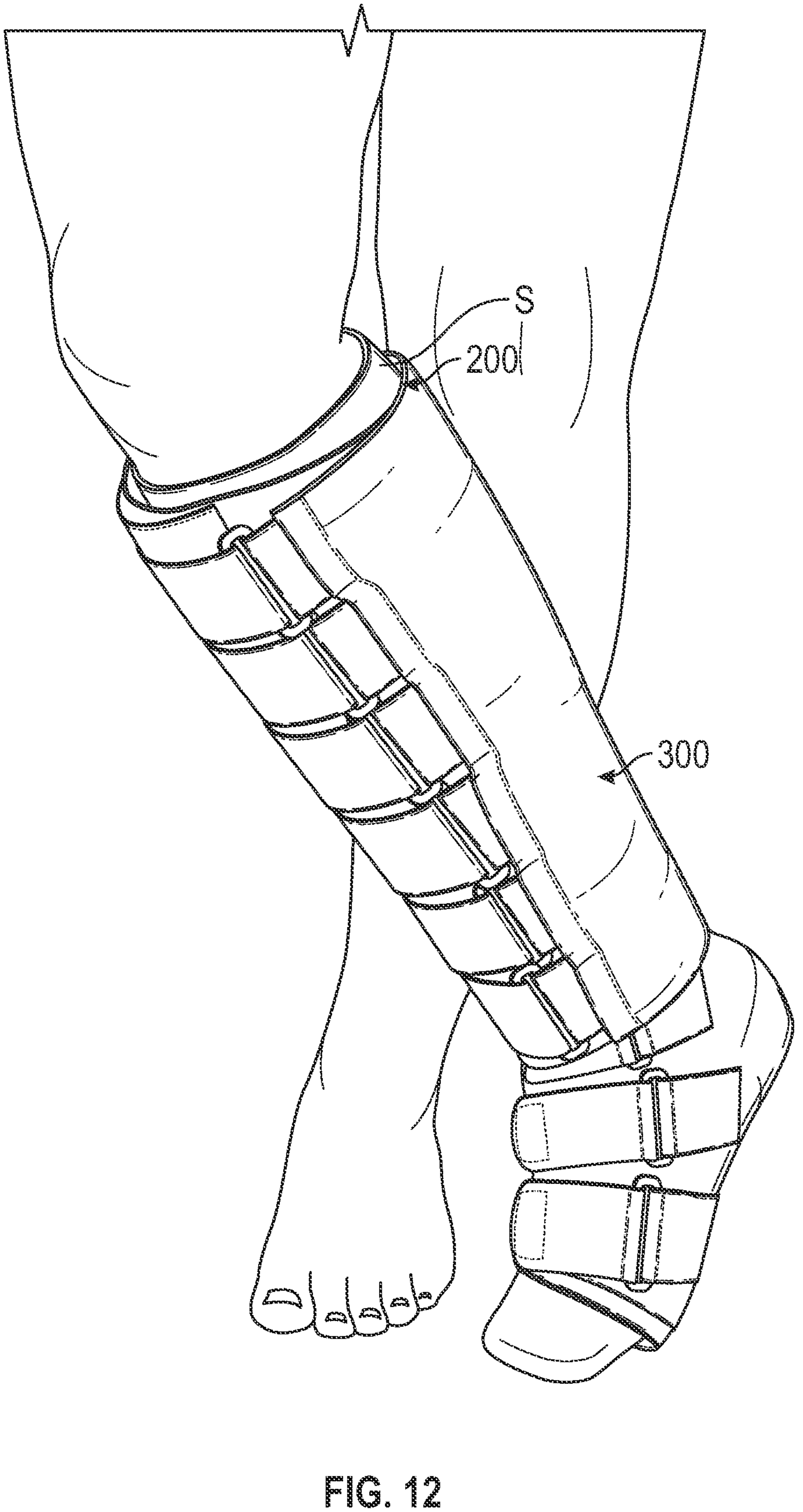
FIG. 12 shows the foam liner of FIG. 11 showing the entire below knee garment.

FIGS. 9-12 show an alternative embodiment with a sleeve design as a liner in a calf or full leg garment. As shown in FIG. 9, a garment or liner 200 is similar to the garment 10 detailed hereinabove, but does not include foam chips. Generally, in the exemplary embodiment shown, the liner 200 include a flat foam or foam with ridges, and is shown as a sleeve 212 with at least one open end (note that in this exemplary embodiment, two open ends 230 and 240 are shown). Generally, the garment 200 is disposed on an extremity, including an upper extremity, a lower extremity, or limb L, such as an arm or leg. The chip sleeve compression garment 200 can be a liner, or can either be used by itself or can be used in combination with other garments, including other compression garments, as shown in FIGS. 10-12. The notch 220 is shown at a lower portion 240 of the garment 200 on a medial portion, but the notch 220 could be included either on the lateral portion or both on the medial portion and lateral portion, or at any other position as desired, including along or otherwise at another portion of the garment 200. The opening or notch 220 can be used to facilitate donning or doffing the garment 200 from the user's limb L. The opening or notch 220 provides a wider opening portion (indicated at 222) to allow for easier fitting on a limb L, including over a wrist, ankle, foot, or hand, or removal from such. For example, the garment 200 could advantageously be designed to closely fit the size of a person's wrist, but the wrist portion of the garment 200 must expand over the hand as the garment 200 is donned and doffed. Similarly, the garment 200 could advantageously be designed to closely fit the size of a person's ankle, the ankle portion of the garment 200 must expand over the foot and heel as the garment 200 is donned and doffed. Additionally, an elastic stretch panel loop portion 250 can be included proximate the opening or notch 220, which, among other benefits, can help keep the opening or notch 220 closed together when the user desires to keep the garment 200 in place on the limb L. The stretch panel 250 preferably is constructed from a material having a lower modulus of elasticity than the fabric comprising the chip sleeve compression garment 200, so that the force to expand the end 240 or portion of the chip sleeve garment 200 having the notch 220 is less than the force to expand the compression garment 200 otherwise fashioned without a notch 220, whereby making it easier to don and doff the garment 200.

In at least one embodiment, the liner 200 could include a notch 220 that extends farther along the length of the liner 200 (not shown). In one instance, the notch 200 could extend essentially the entire length of the liner 200 to allow the liner 200 to widen the opening 222 wider. This extension of the notch 220 could allow easier donning/doffing for a foam liner which may not stretch as readily as a chip sleeve shown hereinabove. In another instance, the liner 200 could include two notches 220 with both notches being on one side of the same end or with a notch on each side of the liner in two ends. A two notch version could include similarly sized notches or could include one notch longer/shorter than another of the notches. More notches could be included as desired. Additionally, multiple notches with similar features could be provided in the chip sleeve detailed herewithin. Further, the stretch panel loop can either be extended or shortened to cover more or less of the notch as needed. Further still, more than one stretch panel loop can be included, e.g. at both ends of the liner or to cover more than one notch if disposed on one end.

The liner 200 can be used in combination with a second compression garment 300 positioned over it. The second compression garment 300 as shown in FIGS. 10-12 includes adjustment straps 210 that allow the second compression garment 300 to be tightened or loosened as desired. As shown in FIGS. 10-12, the liner 200 is provided between a sock S and an outer shell or garment 300.

It will be appreciated by those skilled in the art that changes could be made to the embodiments described above without departing from the broad inventive concept thereof. For example, the garment and/or elastic stretch panel loop portion can include additional features. Additionally, the chip sleeve can be used in other applications, including with other base configurations. For example, the chip sleeve can be used in a design involving a connection at a back seam (see, for example, the regular Compreflex product and Compreflex Reduce, both manufactured by the current assignee. It is understood, therefore, that this disclosure is not limited to the particular embodiments disclosed, but it is intended to cover modifications within the spirit and scope of the present disclosure as defined by the appended claims.

In at least one exemplary embodiment, a chip sleeve garment includes an outer layer of fabric connected to an inner layer of fabric to form a sleeve with a space between the outer layer of fabric and the inner layer of fabric, foam disposed in the space, and two ends, with at least one of the two ends defines an opening, and a notch disposed proximate the opening. The notch is separable such that, when separated by a user, the notch facilitates increasing the size of the opening. In at least one embodiment, the notch can be covered by a stretch portion. In another aspect, the stretch portion can be secured to the outer layer of the garment. In at least one embodiment, the garment can be a compression garment. In at least one embodiment, the garment can be sized to fit over either an upper extremity or a lower extremity of a human. In one example, the upper extremity can be a wrist. In one example, the lower extremity can be an ankle. In at least one embodiment, the garment is a liner capable of being used under a compression garment. In at least one embodiment, the foam is chip foam, flat foam, or foam with ridges.

In one exemplary embodiment, a method of donning or doffing a chip sleeve garment is provided, with the method including providing an outer layer of fabric connected to an inner layer of fabric to form a sleeve with a space between the outer layer of fabric and the inner layer of fabric, the chip sleeve garment including foam disposed in the space, two ends, wherein at least one of the two ends defines an opening, and a notch disposed proximate the opening; and wherein the notch is separable such that, when separate by a user, the notch facilitates increasing the size of the opening, and disposing an open end of the two ends over a portion an upper extremity or a lower extremity of a human. In at least one embodiment of the exemplary method, the foam is chip foam, flat foam, or foam with ridges. In at least one embodiment of the exemplary method, the garment defines a notch disposed proximate each of the openings. In at least one embodiment, the exemplary method further includes separating the garment at the notch to increase a size of the opening. In at least one embodiment of the exemplary method, the garment includes a stretch panel portion attached to the outer layer of fabric. In at least one embodiment of the exemplary method, the stretch panel portion can be opened to uncover the notch and closed to cover the notch. In at least one embodiment of the exemplary method, a second garment can be disposed over the chip sleeve garment. In at least one embodiment of the exemplary method, the second garment is a compression garment with at least one securing strap. In at least one embodiment of the exemplary method, the at least one securing strap can be secured to compress the chip sleeve garment. In at least one embodiment of the exemplary method, the larger opening is sized to at least one securing strap can be loosened. In at least one embodiment of the exemplary method, the chip sleeve garment and the second garment are secured together.

The present disclosure can be understood more readily by reference to the instant detailed description, examples, and claims. It is to be understood that this disclosure is not limited to the specific systems, devices, and/or methods disclosed unless otherwise specified, as such can, of course, vary. It is also to be understood that the terminology used herein is for the purpose of describing particular aspects only and is not intended to be limiting.

The instant description is provided as an enabling teaching of the disclosure in its best, currently known aspect. Those skilled in the relevant art will recognize that many changes can be made to the aspects described, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the instant description is provided as illustrative of the principles of the present disclosure and not in limitation thereof.

As used herein, the singular forms "a," "an" and "the" include plural referents unless the context clearly dictates otherwise. Thus, for example, reference to a "body" includes aspects having two or more bodies unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Although several aspects of the disclosure have been disclosed in the foregoing specification, it is understood by those skilled in the art that many modifications and other aspects of the disclosure will come to mind to which the disclosure pertains, having the benefit of the teaching presented in the foregoing description and associated drawings. It is thus understood that the disclosure is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described disclosure.

The invention claimed is:

1. A chip sleeve garment comprising:

an outer layer of elastic fabric connected to an inner layer of elastic fabric to form a sleeve with a space between the outer layer of fabric and the inner layer of fabric;

foam disposed in the space;

two ends, wherein at least one of the two ends defines an opening; a notch disposed proximate the opening and covered by a stretch portion;

wherein the notch is separable such that, when separated by a user, the notch facilitates increasing the size of the opening.

2. The chip sleeve garment of claim 1 wherein the stretch portion is secured to the outer layer of the garment and completely encircles the outer layer.

3. The chip sleeve garment of claim 1 wherein the stretch portion provides compression to the garment without using straps.

4. The chip sleeve garment of claim 1 wherein the garment is sized to fit over either an upper extremity or a lower extremity of a human.

5. The chip sleeve garment of claim 4 wherein the upper extremity is a wrist.

6. The chip sleeve garment of claim 4 wherein the lower extremity is an ankle.

7. The chip sleeve garment of claim 1 wherein the garment is a liner capable of being used under a compression garment.

8. The chip sleeve garment of claim 1 wherein the foam is chip foam, flat foam, or foam with ridges.

9. A method of donning or doffing a chip sleeve garment comprising:

providing an outer layer of elastic fabric connected to an inner layer of elastic fabric to form a sleeve with a space between the outer layer of fabric and the inner layer of fabric, the chip sleeve garment including foam disposed in the space, two ends, wherein at least one of the two ends defines an opening, and a notch disposed proximate the opening and covered by a stretch portion; and wherein the notch is separable such that, when separate by a user, the notch facilitates increasing the size of the opening; and, disposing an open end of the two ends over a portion of an upper extremity or a lower extremity of a human.

10. The method of claim 9 wherein the foam is chip foam, flat foam, or foam with ridges.

11. The method of claim 10 wherein the garment defines a notch disposed proximate each of the openings.

12. The method of claim 9 further comprising:

separating the garment at the notch to increase a size of the opening.

13. The method of claim 9 wherein the garment includes a stretch panel portion attached to the outer layer of fabric.

14. The method of claim 13 wherein the stretch panel portion completely encircles the outer layer, can be opened to uncover the notch, and can be closed to cover the notch.

15. The method of claim 9 wherein a second garment can be disposed over the chip sleeve garment.

16. The method of claim 15 wherein the second garment is a compression garment with at least one securing strap.

17. The method of claim 16 wherein the at least one securing strap can be secured to compress the chip sleeve garment.

18. The method of claim 17 wherein the opening is sized so the at least one securing strap can be loosened.

19. The method of claim 15 wherein the chip sleeve garment and the second garment are secured together.

* * * * *